United States Patent
Zhou et al.

(10) Patent No.: US 9,376,446 B2
(45) Date of Patent: Jun. 28, 2016

(54) EMISSIVE DENDRIMER COMPOSITION

(75) Inventors: Zhang-Lin Zhou, Palo Alto, CA (US); Gary Gibson, Palo Alto, CA (US); Lihua Zhao, Sunnyvale, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 614 days.

(21) Appl. No.: 13/878,222

(22) PCT Filed: Oct. 7, 2010

(86) PCT No.: PCT/US2010/051858
§ 371 (c)(1),
(2), (4) Date: Apr. 7, 2013

(87) PCT Pub. No.: WO2012/047224
PCT Pub. Date: Apr. 12, 2012

(65) Prior Publication Data
US 2013/0187538 A1    Jul. 25, 2013

(51) Int. Cl.
*C09K 11/06* (2006.01)
*C07D 487/22* (2006.01)
*H05B 33/14* (2006.01)

(52) U.S. Cl.
CPC .............. *C07D 487/22* (2013.01); *C09K 11/06* (2013.01); *H05B 33/14* (2013.01); *H05B 33/145* (2013.01); *C09K 2211/1416* (2013.01); *C09K 2211/1425* (2013.01); *C09K 2211/1466* (2013.01); *G02F 2201/44* (2013.01)

(58) Field of Classification Search
USPC ........................................................ 548/428
See application file for complete search history.

(56) References Cited

U.S. PATENT DOCUMENTS

| 6,579,632 B2 | 6/2003 | Thompson et al. |
| 7,537,842 B2 | 5/2009 | Burn et al. |
| 7,632,576 B2 | 12/2009 | Burn et al. |
| 2003/0165716 A1 | 9/2003 | Samuel et al. |

FOREIGN PATENT DOCUMENTS

WO     2005/061240 A1     7/2005

OTHER PUBLICATIONS

Duan et al., "Nanosized pi-Conjugated Molecules Based on Truxene and Porphyrin: Synthesis and High Fluorescence Quantum Yields", Organic Letters, vol. 7, No. 19, pp. 4071-4074 (published on Web Aug. 13, 2005).*
J. Li et al., "Dendrimers for organic light-emitting diodes," J. of Materials Chem., 2009, 19, 7584-7591, year 2009.
P.L. Burn et al., "The development of light-emitting dendrimers for displays," Advanced Materials 2007, 19, 1675-1688, year 2009.
S. Drouet et al., "Fluorenyl dendrimer porphyrins: synthesis and photophysical properties," Tetrahedron 65 (2009) 10693-10700, year 2009.
X. Wang et al., "Zinc tetraphenylporphyrin-fluorene branched copolymers: synthesis and light-emitting properties," Macromolecules 2010, 43, 709-715, dated Dec. 28, 2009.
J. Zhao et al., "Synthesis and photocurrent response of porphyrin-containing conjugated polymers," Chinese Science Buleetin 2006, vol. 51, No. 11, 1287-1295, dated 2006.
International search report and written opinion in priority PCT patent application, PCT/US2010/051858, dated Aug. 2, 2011.

* cited by examiner

*Primary Examiner* — Marie R. Yamnitzky
(74) *Attorney, Agent, or Firm* — Thorpe, North & Western L.L.P.

(57) ABSTRACT

The present disclosure is directed towards emissive dendrimer compositions, luminescence-based pixels, luminescence-based sub-pixels, and associated methods with an emissive dendrimer having various structures as described herein.

15 Claims, 4 Drawing Sheets

EMISSIVE DENDRIMER COMPOSITION

BACKGROUND

A reflective display is a non-emissive device in which ambient light is used for viewing the displayed information. Rather than modulating light from an internal source, desired portions of the incident ambient light spectrum are reflected from the display back to a viewer. Electronic paper (e-paper) technologies have evolved to provide single layer monochromatic displays that control the reflection of ambient light. Luminescence-based materials provide alternative, more efficient pathways for utilizing ambient light in reflective displays, thereby making bright, full color reflective displays possible.

DETAILED DESCRIPTION

Figure 1:
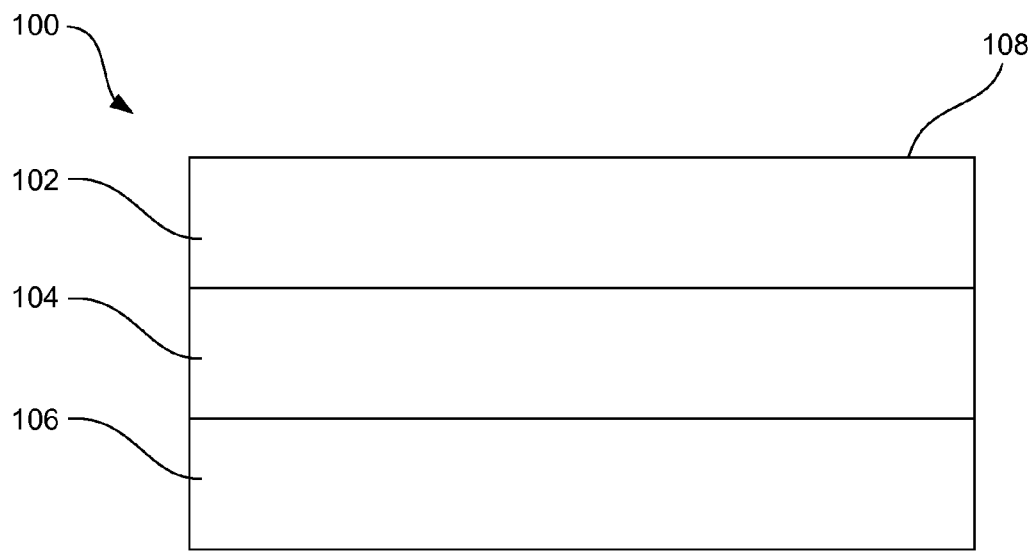
FIG. 1 is a cross-sectional schematic view of a luminescence-based sub-pixel in accordance with an example of the present disclosure.

Before the present invention is disclosed and described, it is to be understood that the present disclosure is not limited to the particular process steps and materials disclosed herein because such process steps and materials may vary somewhat. It is also to be understood that the terminology used herein is used for the purpose of describing particular examples only. The terms are not intended to be limiting because the scope of the present disclosure is intended to be limited only by the appended claims and equivalents thereof.

It is be noted that, as used in this specification and the appended claims, the singular forms "a," "an," and "the" include plural referents unless the context clearly dictates otherwise.

As used herein, "alkyl" refers to a branched, unbranched, or cyclic saturated hydrocarbon group, which typically, although not necessarily, contains from 1 to about 50 carbon atoms, or 1 to about 40 carbon atoms, or 1 to about 30 carbon atoms for example. Alkyls include, but are not limited to, methyl, ethyl, n-propyl, isopropyl, n-butyl, isobutyl, t-butyl, octyl, and decyl, for example, as well as cycloalkyl groups such as cyclopentyl, and cyclohexyl, for example. The term "lower alkyl" refers to an alkyl group having from 1 to 6 carbon atoms. The term "higher alkyl" refers to an alkyl group having more than 6 carbon atoms, for example, 7 to about 50 carbon atoms, or 7 to about 40 carbon atoms, or 7 to about 30 carbon atoms or more. As used herein, "substituted alkyl" refers to an alkyl substituted with one or more substituent groups. The term "heteroalkyl" refers to an alkyl in which at least one carbon atom is replaced with a heteroatom. If not otherwise indicated, the term "alkyl" includes unsubstituted alkyl, substituted alkyl, lower alkyl, and heteroalkyl.

As used herein, "aryl" refers to a group containing a single aromatic ring or multiple aromatic rings that are fused together, directly linked, or indirectly linked (such that the different aromatic rings are bound to a common group such as a methylene or ethylene moiety). Aryl groups described herein may contain, but are not limited to, from 5 to about 50 carbon atoms, or 5 to about 40 carbon atoms, or 5 to 30 carbon atoms or more. Aryl groups include, for example, phenyl, naphthyl, anthryl, phenanthryl, biphenyl, diphenylether, diphenylamine, and benzophenone. The term "substituted aryl" refers to an aryl group substituted with one or more substituent groups. The term "heteroaryl" refers to an aryl group in which at least one carbon atom is replaced with a heteroatom. If not otherwise indicated, the term "aryl" includes unsubstituted aryl, substituted aryl, and heteroaryl.

As used herein, "substituted" means that a hydrogen atom of a compound or moiety is replaced by another atom such as a carbon atom or a heteroatom, which is part of a group referred to as a substituent. Substituents include, for example, alkyl, alkoxy, aryl, aryloxy, alkenyl, alkenoxy, alkynyl, alkynoxy, thioalkyl, thioalkenyl, thioalkynyl, and thioaryl.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

It has been recognized that it would be advantageous to develop emissive dendrimers suitable for a wide variety of applications. In accordance with this, compositions, devices, and methods described herein can include emissive dendrimers that can absorb and emit various wavelengths of light. As such, the present disclosure can provide emissive dendrimers that can be used in luminescence-based sub-pixels and luminescence-based pixels. It is noted that when discussing the present compositions, devices and methods, each of these discussions can be considered applicable to each of these examples, whether or not they are explicitly discussed in the context of that example. Thus, for example, in discussing an emissive dendrimer used in a luminescence-based sub-pixel, such an emissive dendrimer can also be used in a luminescence-based pixel or a method for illuminating a display, and vice versa.

In light of the above, an emissive dendrimer can have the structure:

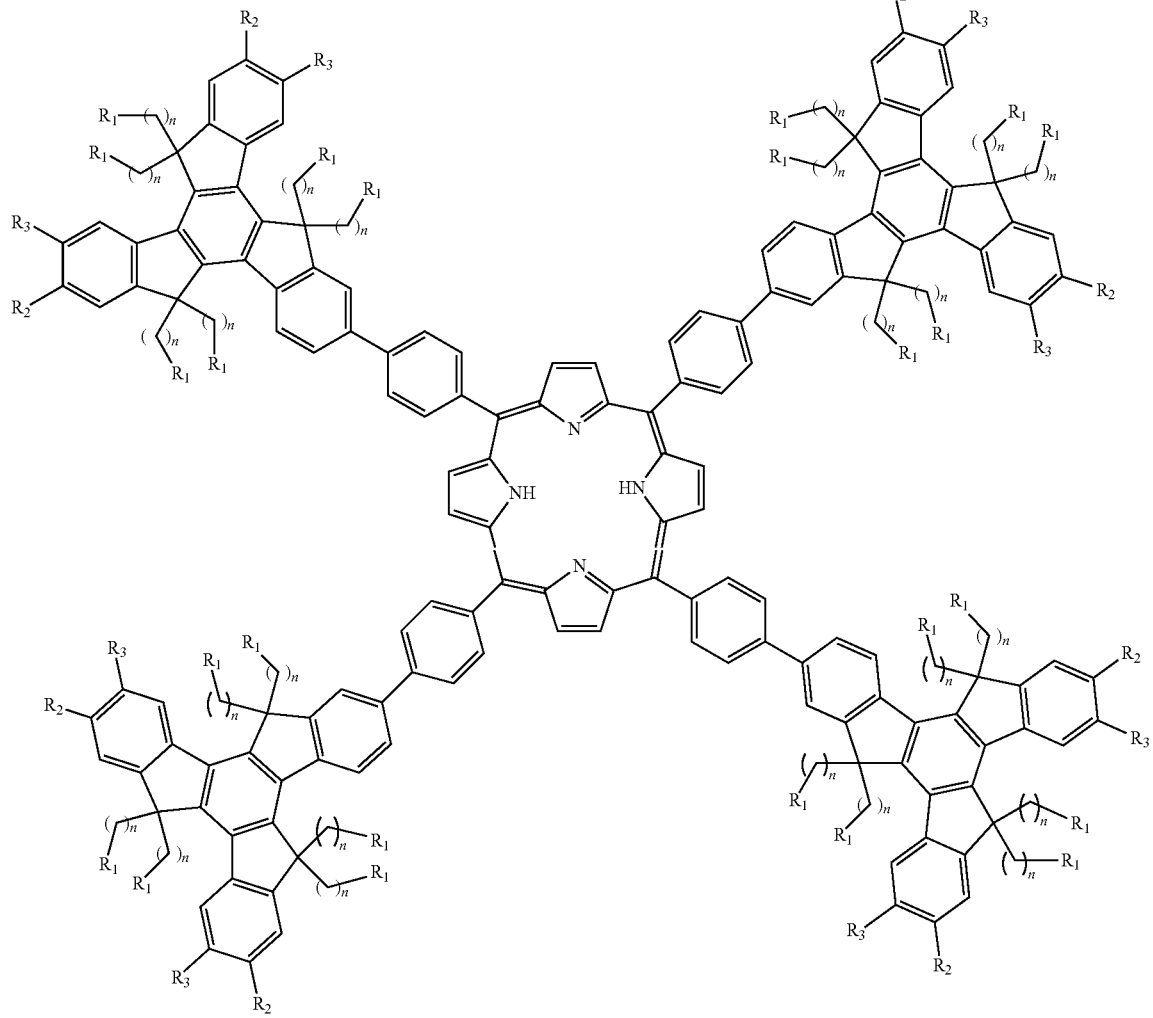

where $R_1$, $R_2$, and $R_3$ are independently selected from the group of $COOZ$, $SO_3Z$, $PO_3Z$, $N(R)_3^+Y^-$, and $(CH_2CH_2O)_mCH_3$; Z is independently selected from the group of hydrogen, a monovalent metal ion, and $N(R)_4^+$; R is independently selected from the group of hydrogen, alkyl, and aryl; $Y^-$ is selected from the group of a halogen, sulfate, and sulfonate; m ranges from 1 to 500, and n independently ranges from 1 to 30. The emissive dendrimer generally absorbs energy in the form of electromagnetic radiation. Additionally, the emissive dendrimer can transfer the energy to another luminophore via a resonant energy transfer mechanism as discussed herein, or can emit the energy in the form of light, as discussed herein.

In one example, the emissive dendrimer can be part of a composition that includes a matrix. The matrix can comprise an emissive dendrimer and inert, transparent host polymers or cross-linked polymers. Additionally, the emissive dendrimer composition can include a luminophore. The emissive dendrimer compositions described herein can be used to form films. Generally, films can be made by processes such as spin-casting, drop-casting, or jet-printing, after which the solvent is removed via evaporation (which may be accelerated by heating).

Additionally, a luminescence-based sub-pixel can comprise a light shutter with adjustable transmission; a luminescent layer disposed below the light shutter, the luminescent layer containing a matrix including an emissive dendrimer; and a mirror disposed below the luminescent layer for reflecting light emitted from the emissive dendrimer. The emissive dendrimer can be any as described herein.

Further, a luminescence-based pixel can comprise three luminescence-based sub-pixels as described herein, wherein each luminescence-based sub-pixel corresponds to a different color of emitted light such that the luminescence-based pixel can emit light over a spectrum of 300 nm to 800 nm.

Various modifications and combinations that can be derived from the present disclosure and illustrations, and as such, the following figures should not be considered limiting.

Turning now to FIG. 1, a luminescence-based sub-pixel 100 can comprise a shutter 102, a luminescent layer 104, and a mirror 106. The shutter 102 can form the top layer of the sub-pixel, and ambient light for illumination can enter the sub-pixel through the shutter. The shutter can have a light transmission that is adjustable. The shutter can modulate the intensity of ambient light entering the sub-pixel and also the light leaving the sub-pixel. In this way, the shutter can control the amount of light produced by the sub-pixel to achieve the desired brightness. In some examples, the shutter can comprise an electro-optic shutter, the transparency of which can be modulated from mostly transparent to mostly opaque, over some range of wavelengths and with some number of intermediate gray levels. There are a number of possible choices for the electro-optic shutter, including black/clear dichroic-liquid crystal (LC) guest-host systems and in-plane electrophoretic (EP) systems. If a dichroic LC system is used, in some examples, a quarter-wave plate may be disposed between the liquid crystal shutter and the luminescent material. Other options include cholesteric liquid crystal cells, in-plane electrophoretic devices, or electrowetting layers.

The luminescent layer 104 can include an emissive dendrimer. As discussed herein, generally, the emissive dendrimer has the structure shown below:

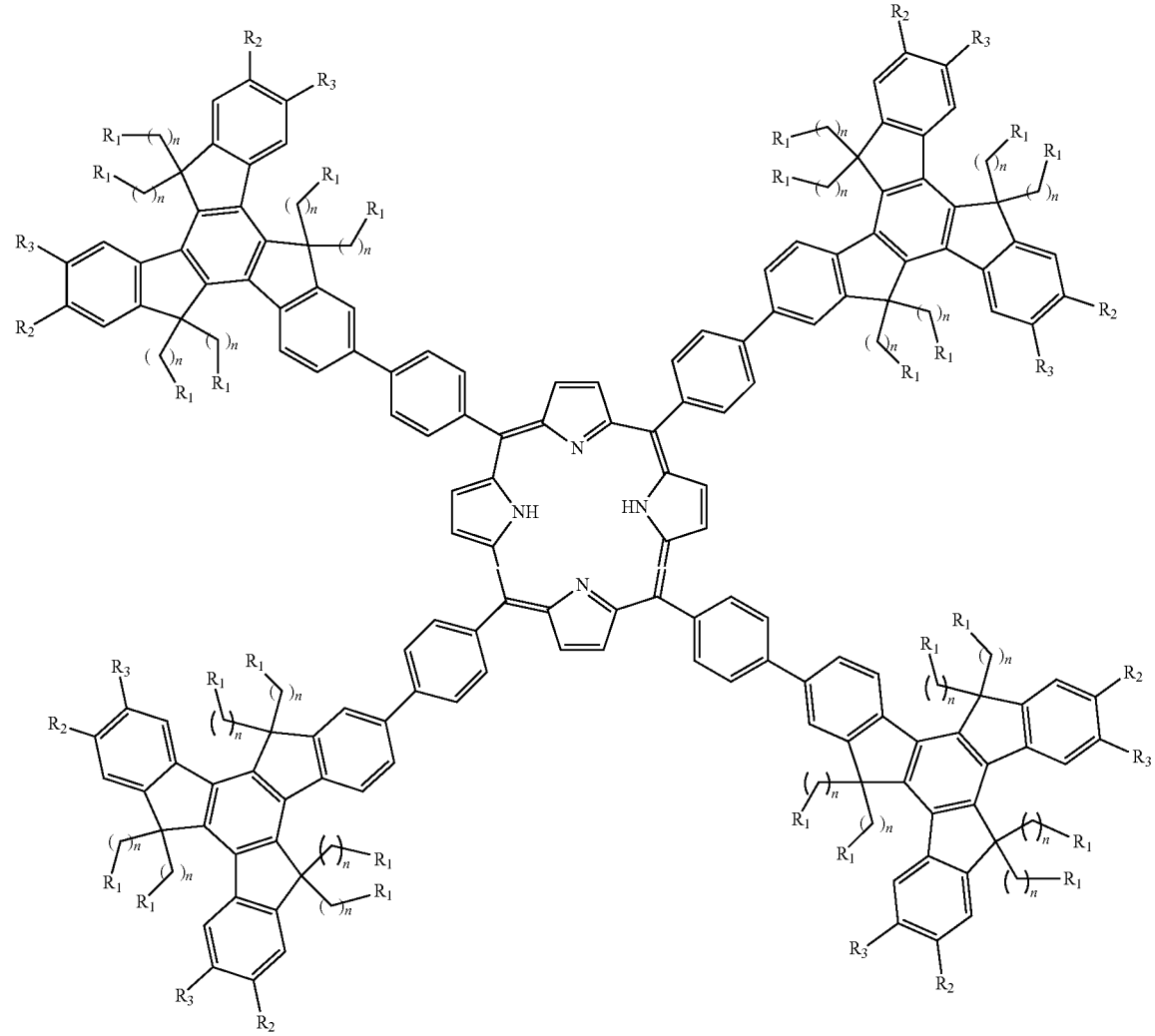

where $R_1$, $R_2$, and $R_3$ are independently selected from the group of COOZ, $SO_3Z$, $PO_3Z$, $N(R)_3^+Y^-$, and $(CH_2CH_2O)_mCH_3$; Z is independently selected from the group of hydrogen, a monovalent metal ion, and $N(R)_4^+$; R is independently selected from the group of hydrogen, alkyl, and aryl; $Y^-$ is selected from the group of a halogen, sulfate, and sulfonate; m ranges from 1 to 500, and n independently ranges from 1 to 30. In one example, $R_1$, $R_2$, and $R_3$ can be salts independently selected from $N(H)_3^+Y$, $SO_3Z$, and $PO_3Z$, where Y and Z are ionic. In another example, n can range from 5 to 12. Additionally, in one example, $R_1$, $R_2$, and $R_3$ can be $(CH_2CH_2O)_mCH_3$ where m can be from 30 to 50.

In addition to the emissive dendrimer, the present compositions can further comprise a luminophore. The luminophores described herein can include without limitation organic dyes; inorganic dyes; phosphors; semiconducting nanoparticles; pigment particles containing luminescent dye molecules, oligomers, or polymers; and mixtures thereof. In one example, the luminophore can be selected from a 4,4-difluoro-4-bora-3a,4a-diaza-s-indacene (BODIPY) dye, a rhodamine dye, a fluorine dye, a sulforhodamine dye, and mixtures thereof. In one aspect, the luminophore can be sulforhodamine 640, CAS#60311-02-6. Generally, the luminophore can be present in the luminescent layer from about 0.01% to about 10% by weight. In one example, the luminophore can be present in the luminescent layer from about 0.05% to about 2% by weight.

Generally, the luminescent layer includes a matrix. Typically, the emissive dendrimers can be dispersed in the matrix. As discussed herein, the matrix generally includes an emissive dendrimer and a transparent host polymer. Additional materials that can be present include other luminophores and other radiation absorbers including emissive and non-emissive radiation absorbers. As also discussed herein, the emissive dendrimer and other emissive materials can absorb energy in the form or electromagnetic radiation and transfer the energy to a luminophore via a resonant energy transfer mechanism, e.g., via Förster exchange. Generally, non-emissive radiation absorbers can absorb unwanted wavelengths. Such materials include anti-oxidants or other non-emissive radiation absorbers, e.g., UV absorbers, used to protect the luminescent dyes from photo-oxidation, thereby making them more robust and photofast. The examples of anti-oxidants can include any sterically hindered amines, substituted phenols and nitro substituted aromatic compounds such as N-methylmorphine, N-methyl morphine oxide, nitrobenzene, 9-nitroanthracene, 2,2'-dinitrobiphenyl, 2,2,6,6-tetramethylpiperidine, N-phenyl-1-napthylane, 2,4,6-tertbutylphenol, etc.

The electromagnetic radiation can be ultraviolet (UV), infrared (IR), and/or visible electromagnetic radiation. In one example, the electromagnetic radiation can have a wavelength of 300 nm to 800 nm. In another example, the electromagnetic radiation can be ambient light. The radiation absorbers can include emissive polymers, dyes, or other radiation absorbing materials. In one example, the radiation absorbers can be emissive polymers including, without limitation, poly(9,9'-dioctylfluorene-co-benzothiadiazole); poly [2-methoxy-5-(2'-ethyl-hexyloxy)-1,4-phenylene vinylene]; polyfluorenes; substituted polyfluorenes; polycarbazoles; substituted polycarbazoles; co-polymers of fluorene and carbazole; co-polymers of fluorene and benzothiadiazole; copolymers of fluorene and phenothiazine; and mixtures thereof. In another example, the radiation absorber can include organic dyes, inorganic phosphors, and/or semiconducting nanocrystals. In one aspect, the radiation absorber can include without limitation perylenes, pyromethenes, rhodamines, sulforhodamines, coumarins, aluminum quinoline complexes, porphyrins, porphins, indocyanine dyes, phenoxazine derivatives, phthalocyanine dyes, polymethyl indolium dyes, polymethine dyes, guaiazulenyl dyes, croconium dyes, polymethine indolium dyes, metal complex IR dyes, cyanine dyes, squarylium dyes, chalcogeno-pyryloarylidene dyes, indolizine dyes, pyrylium dyes, quinoid dyes, quinone dyes, azo dyes, and mixtures and derivatives thereof. Non-limiting examples of specific porphyrin and porphyrin derivatives can include etioporphyrin 1 (CAS 448-71-5), deuteroporphyrin IX 2,4 bis ethylene glycol (D630-9) available from Frontier Scientific, and octaethyl porphrin (CAS 2683-82-1), azo dyes such as Mordant Orange CAS 2243-76-7, Methyl Yellow (60-11-7), 4-phenylazoaniline (CAS 60-09-3), Alcian Yellow (CAS 61968-76-1), available from Aldrich chemical company, and mixtures thereof. In one aspect, the radiation absorber can include without limitation quinoline dyes, porphyrins, porphins, and mixtures and derivatives thereof.

Additionally, the matrix can include a mixture of various radiation absorbers. The radiation absorbers and/or emissive dendrimer can be present in the luminescent layer from about 0.01% to about 99.99% by weight. In one example, the radiation absorbers and/or emissive dendrimer can be present in the luminescent layer from about 0.05% to about 2% by weight. The ratio of luminophore to emissive dendrimer and/or emissive radiation absorber can be 10:1 to 1:10 by weight. In one aspect the ratio can be 2:1 to 1:2 by weight.

The luminophore can be chosen to match an emissive energy level of the emissive dendrimer and/or radiation absorber, where the emissive dendrimer acts as an energy absorber and transfers the energy to the luminophore as discussed herein. Generally, matching refers to matching the luminophore's absorption wavelengths to the dendrimer's and/or radiation absorber's emission wavelength. The matching can provide an overlap between these wavelength ranges allowing for energy transfer between the emissive dendrimer and/or the radiation absorber and the luminophore via a resonant energy transfer mechanism as discussed herein, such as Förster exchange mechanism. In one example, the emissive dendrimer and/or the radiation absorber can absorb electromagnetic radiation having a wavelength of 300 nm to 800 nm. Additionally, in one example, the luminophore can be used to transfer energy to the emissive dendrimer. As such, the emissive dendrimer can be chosen to match an emissive energy level of the luminophore, which transfers energy to the emissive dendrimer.

The luminescent layer can absorb some, but not necessarily all, light with wavelengths shorter than an absorption edge, $\lambda_{abs}$, with a substantial fraction of the absorbed energy re-radiated by the luminophore in a band around an emission wavelength $\lambda_{emis}$ that is longer than the absorption edge. This can provide a large advantage in efficiency over devices that merely reflect a portion of the spectrum of the incident light. A large fraction of the incident energy at wavelengths below the absorption wavelength (including UV) can be utilized rather than just the small portion that falls within the particular reflected color band. For example, in the case of a red sub-pixel, this can provide a several-fold improvement in brightness for a given sub-pixel area. In general, it is desirable to use a luminescent layer whose absorption extends from some cutoff, $\lambda_{abs}$, down to the shortest wavelengths available in typical ambient environments. In practice, there might be negligible benefit in absorbing much below 320 nm, although somewhat shorter wavelengths may contribute in outdoor environments if the top layers of the pixels and sub-pixels are reasonably transparent in this region.

The matrix can include other polymers in which the emissive dendrimer and/or luminophore can be dispersed, including the transparent polymers as discussed above. Such inert transparent polymers do not provide energy transfer but can be added to the matrix in addition to the energy transfer materials. For example, a matrix can include a transparent polymer, a radiation absorber, and an emissive dendrimer. The transparent polymer can include, without limitation, alkly polyacrylate, alkyl polymethacrylate, cross-linked alkly polyacrylate, poly(methyl methacrylate), polycarbonate, polystyrene, polyethylene terephthalate, polyethylene naphthalate, polyvinyl alcohol, and mixtures thereof. In one example, the luminophore can be miscible and/or soluble with any solvent present in the matrix or used before film formation of the luminescent layer. In another example, the emissive dendrimer can be soluble with any solvent present in the matrix or used before film formation of the luminescent layer. Additionally, in one example, the luminophore can be miscible with the emissive dendrimer. Further, in another example, the emissive dendrimer can be soluble in water and/or alcohol.

Such compatibility of the emissive dendrimers and the matrix can improve emission efficiency of the emissive dendrimer compositions described herein, including the present luminescent layers, by preventing or minimizing luminescence quenching of the emissive dendrimers from agglomeration.

The matrix can also include solvents, e.g., those used prior to film formation. In one example, the solvent can be an organic solvent. In one aspect, the solvent can be an alcohol. In another example, the solvent can be water. Solvents than can be used include, without limitation, chloroform, chlorobenzene, toluene, alcohols, and other organic solvents such as benzene, xylenes, iso-propanol, iso-hexafluoropropanol, ethyl acetate, cyclohexanes, dodecanes, isopars, dimethylformamide, dimethyl sulfoxide, N-methylpyrrolidone etc.

Figure 2:
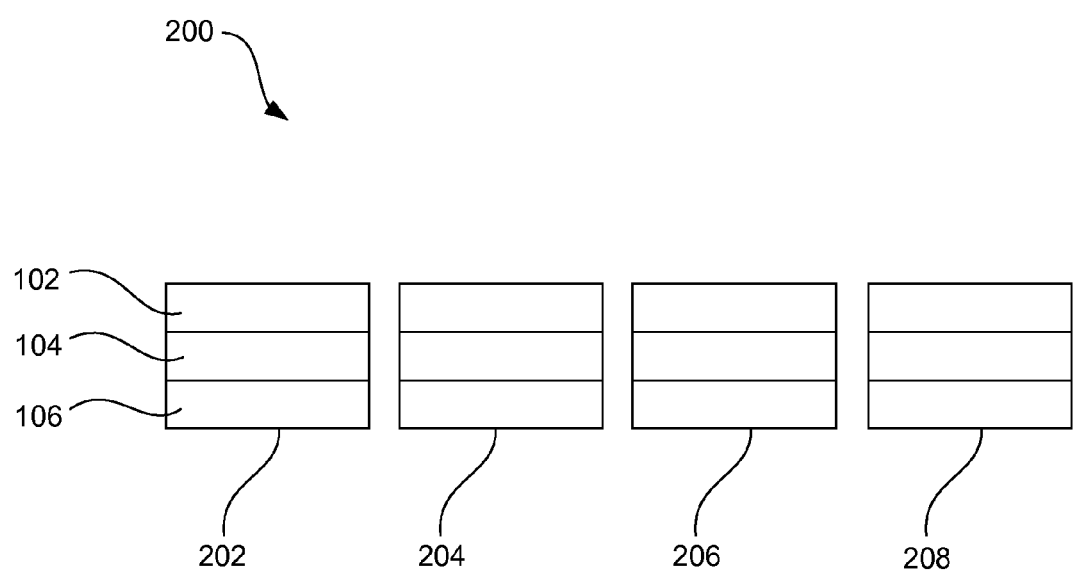
FIG. 2 is a cross-sectional schematic view of a luminescence-based pixel in accordance with an example of the present disclosure.

Below the luminescent layer, the sub-pixel can include a mirror 106 that reflects a selected portion of the optical spectrum. This mirror can be, for example, a Bragg stack, an absorbing dye over a broadband mirror, or a layer of wavelength-selective optical scatterers, such as plasmonic particles. The latter two options may be beneficial in terms of the ease with which mirrors with different reflection bands can be manufactured in a side-by-side sub-pixel configuration (as shown in FIG. 2). They also may be chosen for their reduced dependence on the angle of incidence of the ambient light.

The mirror can be wavelength-selective in that it reflects only light in a selected bandwidth. The reflection bandwidth may be chosen so that the mirror reflects light of the primary color of the sub-pixel but does not reflect other wavelengths. In other cases, the mirror may reflect wavelengths that are absorbed by the luminescent layer as well as wavelengths that contribute to the desired color of the sub-pixel. For example, the mirror for a green sub-pixel can reflect green and blue light but may not reflect any red portion of the incident light. Similarly, the mirror for a blue sub-pixel may reflect blue, and perhaps near UV wavelengths, but not red or green wavelengths. The mirror can enhance the performance of the color sub-pixel in three regards.

In one example, mirror can re-direct light that is emitted by the luminophore and/or emissive dendrimer away from the viewing surface 108. By reflecting the emitted light back toward the viewing surface, the total amount of light from the sub-pixel available for viewing can be significantly increased. In this regard, with a reasonable Stokes shift ($\lambda_{emis}-\lambda_{abs}$) separating the absorption edge and the emission wavelength of the luminescent layer, the luminophore and/or emissive dendrimer will not significantly re-absorb the reflected emitted light as it passes back through the luminescent layer and out of the viewing surface.

In another example, the wavelength-selective mirror can enable one to take optimum advantage of the portion of incident ambient light not significantly absorbed by the luminescent layer but with wavelengths that contribute to the creation of the desired color. This portion, which, in general, includes light with wavelengths between $\lambda_{abs}$ and $\lambda_{emis}$ (i.e., within the Stoke shift range) and somewhat beyond $\lambda_{emis}$, will reach the mirror. Some of this light may then be reflected back toward the viewing surface so that it contributes to the overall output of the sub-pixel. Without the mirror, this light is wasted. In some examples, the reflection band of the mirror can be chosen such that it starts at a cut-off wavelength longer than the emission wavelength, and extends to shorter wavelengths that include the absorption edge wavelength $\lambda_{abs}$ of the luminescent layer. The long-wavelength cut-off of the mirror reflection can be set at the long-wavelength edge of the color band assigned to that sub-pixel. For example, for a red sub-pixel, the reflection band may reach or even go beyond the long-wavelength edge of the standard range of red, as it may be desirable to reflect red out to the limits of human perception. In some examples, a diffusive mirror may be used to randomize the direction of propagation of the emitted light each time it is reflected by the mirror. Diffusive mirrors can be made that scatter the reflected light within a desired characteristic angular range.

The luminescent layer can be configured to emit a specific color of light. The color can be any color including without limitation red, blue, green, cyan, yellow, magenta, etc. In one example, the luminophore and/or emissive dendrimer can emit light at a wavelength from 600 to 800 nm corresponding to a red color. In another example, the luminophore and/or emissive dendrimer can emit light at a wavelength from 500 to 600 corresponding to a green color. In yet another example, the luminophore and/or emissive dendrimer can emit light at a wavelength from 400 to 500 corresponding to a blue color.

The luminescent layer can have high emission efficiency. In one example, the internal emission efficiency can be greater than 80% when the emissive dendrimer and/or luminophore is present in the matrix at a concentration of about 0.1% to about 1% by weight. Additionally, the emissive dendrimer composition can have a Förster energy transfer efficiency of 95% or more.

While the present discussion has been generally referenced in the context of FIG. 1, it is noted that the above examples are equally applicable to the emissive dendrimer compositions, luminescence-based pixels, and associated methods discussed herein as well.

Turning now to FIG. 2, a luminescence-based pixel 200 can comprise 3 colored sub-pixels, 202, 204, and 206 in a side-by-side architecture. Each sub-pixel can correspond to a specific color of light. For example, sub-pixel 202 can be a red sub-pixel, sub-pixel 204 can be a green sub-pixel, and sub-pixel 206 can be a blue sub-pixel. Additionally, the luminescence-based pixel can include additional sub-pixels. For example, the luminescence-based pixel can include sub-pixel 208, corresponding to white. It is noted that the luminescence-based sub-pixels, similar to as described in FIG. 1, comprise a shutter 102, a luminescent layer 104, and a mirror 106. It is understood that the number of sub-pixels can vary according to the needs of the respective application. In one example, the luminescence-based pixel can be part of a reflective display. Additionally, the luminescence-based pixel comprising three luminescence-based sub-pixels, where each luminescence-based sub-pixel corresponds to a different color of emitted light, can emit light over a spectrum of 300 nm to 800 nm. Further, the luminescent layer can have a thickness of less than 10 μm.

Figure 3:
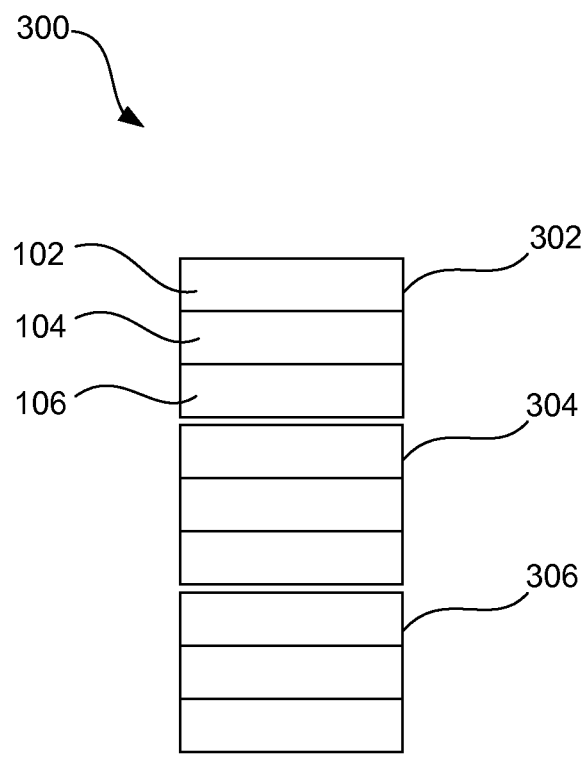
FIG. 3 is a cross-sectional schematic view of another luminescence-based pixel in accordance with an example of the present disclosure.

Turning now to FIG. 3, a luminescence-based pixel 300 can comprise 3 colored sub-pixels, 302, 304, and 306 in a stacked architecture. Each sub-pixel can correspond to a specific color of light. For example, sub-pixel 302 can be a red sub-pixel, sub-pixel 304 can be a green sub-pixel, and sub-pixel 306 can be a blue sub-pixel. Additionally, the luminescence-based pixel can include additional sub-pixels. Again, it is noted that the luminescence-based sub-pixels, similar to as described in FIG. 1, comprise a shutter 102, a luminescent layer 104, and a mirror 106. It is understood that the number of sub-pixels can vary according to the needs of the respective application. In one example, the luminescence-based pixel can be part of a reflective display. Additionally, the luminescence-based pixel comprising three luminescence-based sub-pixels, where each luminescence-based sub-pixel corresponds to a different color of emitted light, can emit light over a spectrum of 300 nm to 800 nm. The stacked architecture can include electrodes, electrode layers, liquid crystal alignment layers, guest-host layers including dichroic dye (the guest) dissolved in a liquid crystal (LC) host, etc (not shown).

Figure 4:
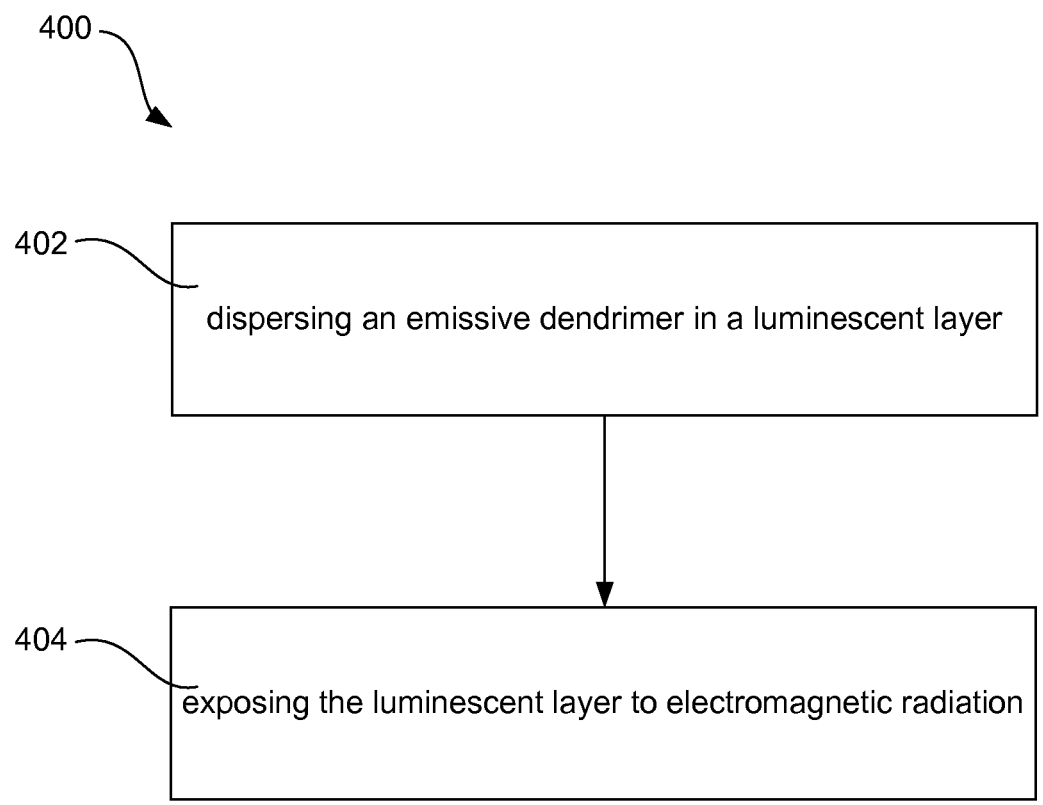
FIG. 4 is a flow chart setting forth a method in accordance with an example of the present disclosure.

In FIG. 4, a method 400 for illuminating a display is set forth and can comprise dispersing an emissive dendrimer in a luminescent layer 402 and exposing the luminescent layer to electromagnetic radiation 404. As previously discussed, the emissive dendrimer can be any as described herein. Additionally, in one example, the method can further comprise forming the luminescent layer by evaporating a solvent mixture of the emissive dendrimer. Such a method step can provide a luminescent layer in the form of a film. Further, in another example, the method can comprise providing a shutter and a mirror as described herein.

EXAMPLES

The following examples illustrate some examples of the present emissive dendrimer compositions, luminescence-based pixels, luminescence-based sub-pixels, and methods that are presently known. However, it is to be understood that the following are only exemplary or illustrative of the application of the principles of the present compositions, devices, and methods. Numerous modifications and alternative compositions, methods, and devices may be devised by those skilled in the art without departing from the spirit and scope of the present compositions and methods. The appended claims are intended to cover such modifications and arrangements. Thus, while the present emissive dendrimer compositions, luminescence-based pixels, luminescence-based sub-pixels, and methods have been described above with particularity, the following examples provide further detail in connection with what are presently deemed to be the acceptable examples.

Example 1

Synthesis of Emissive Dendrimer

An emissive dendrimer is prepared by reacting the substituted fused fluorene (compound 1) with pyrrole and 2,3-dichloro-5,6-dicyanobenzoquinone (DDQ), followed by treatment with triethylamine provides the emissive dendrimer (compound 2), according to the following reaction scheme:

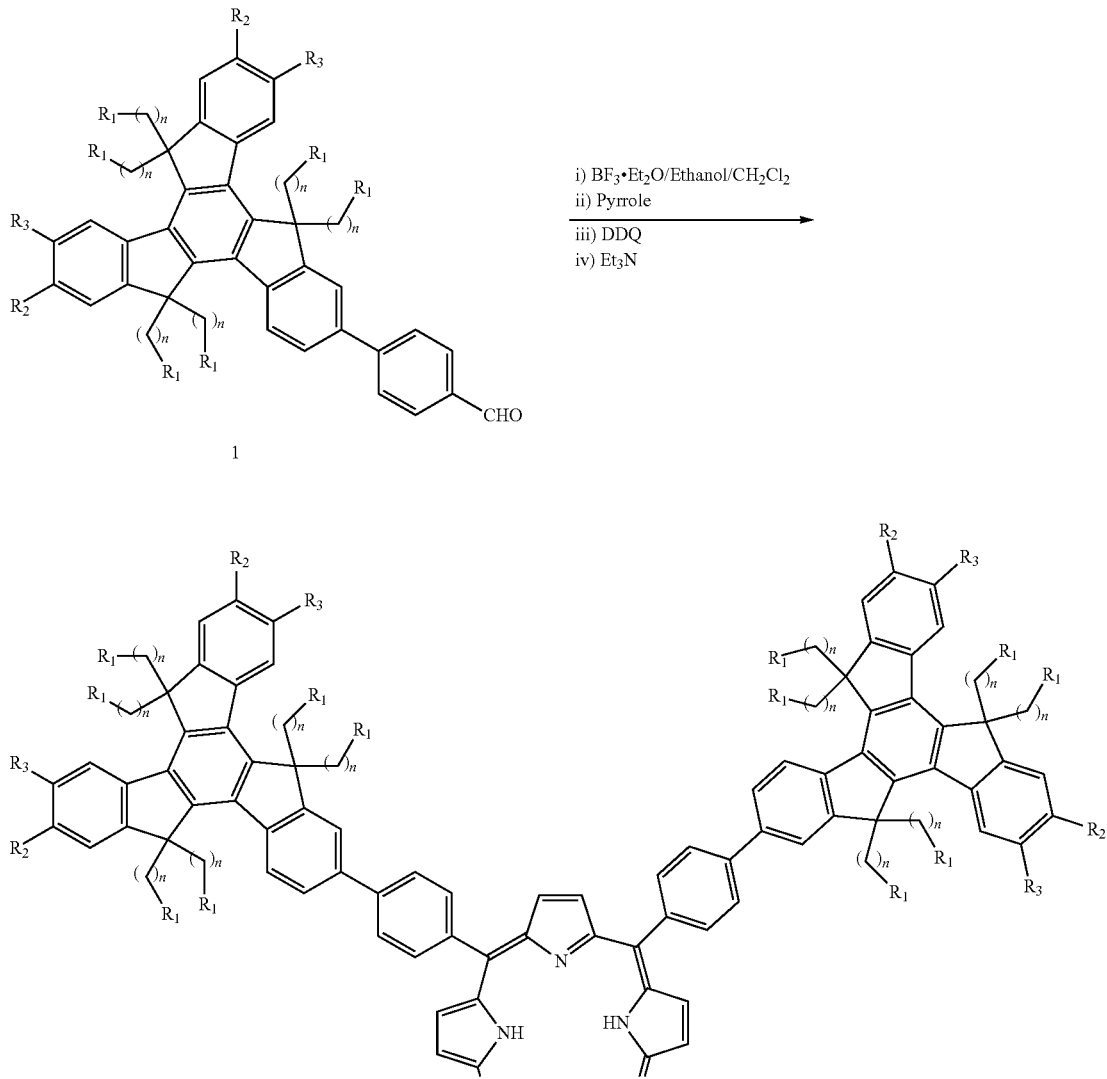

-continued

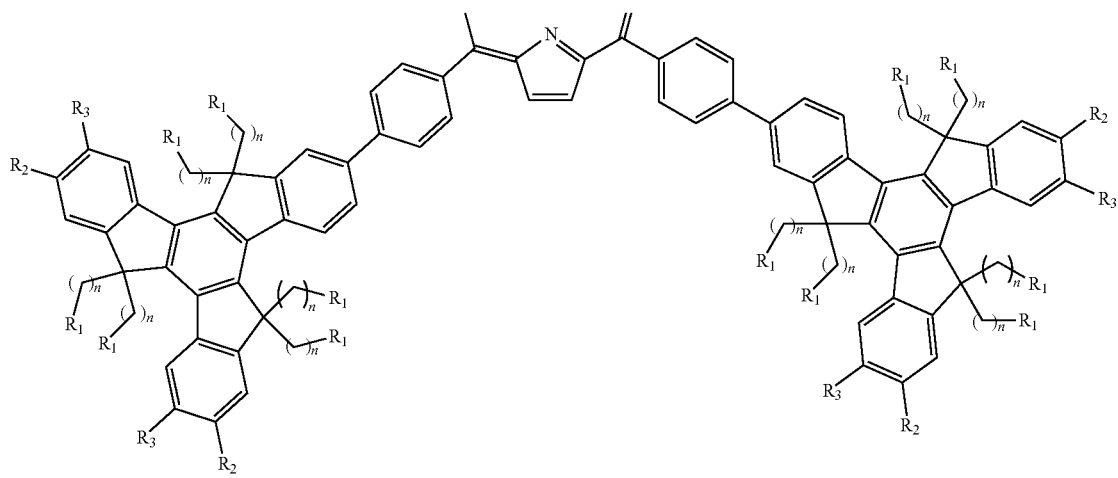

Example 2

Synthesis of Emissive Dendrimer Composition

An emissive dendrimer composition is prepared by admixing the emissive dendrimer of Example 1 in poly(methyl acrylate) in toluene providing approximately 1% of the emissive dendrimer in the polymer by weight. The mixture is then sonicated for one hour. The composition is spin cast, followed by evaporation of the solvent, to form an emissive dendrimer film.

While the disclosure has been described with reference to certain examples, those skilled in the art will appreciate that various modifications, changes, omissions, and substitutions can be made without departing from the spirit of the disclosure. It is intended, therefore, that the present disclosure be limited only by the scope of the following claims.

What is claimed is:

1. An emissive dendrimer composition, comprising an emissive dendrimer having the structure:

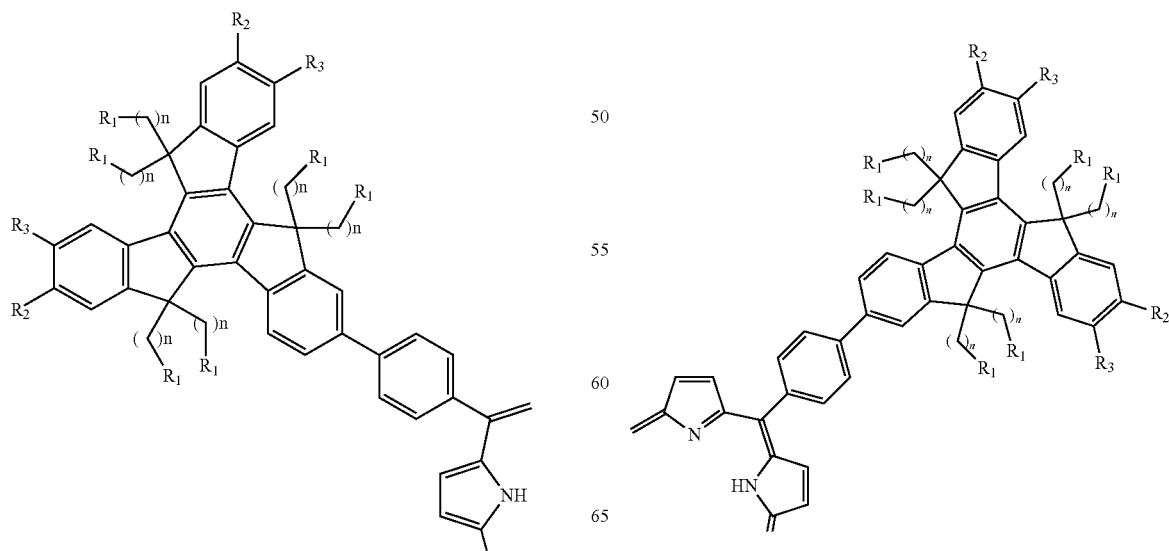

-continued

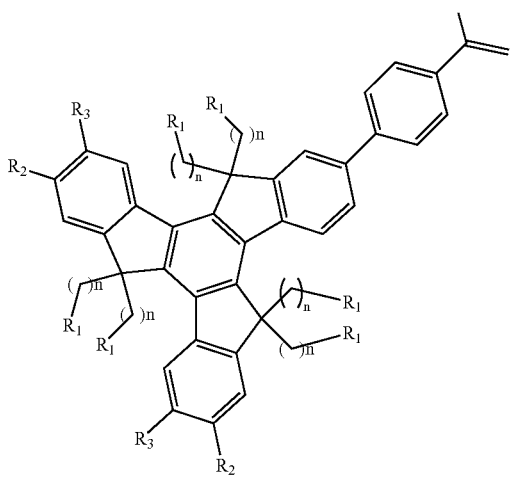

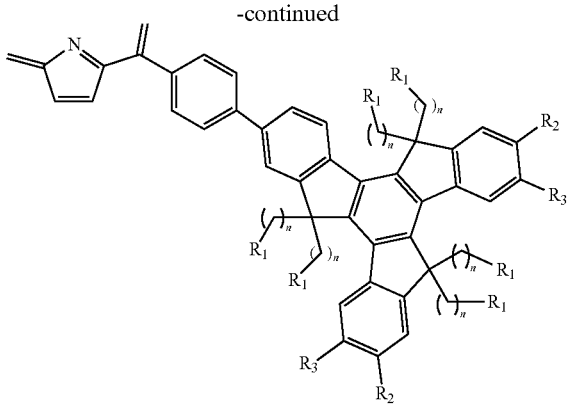

where $R_1$, $R_2$, and $R_3$ are independently selected from the group of COOZ, $SO_3Z$, $PO_3Z$, $N(R)_3^+Y^-$, and $(CH_2CH_2O)_mCH_3$; Z is independently selected from the group of hydrogen, a monovalent metal ion, and $N(R)_4^+$; R is independently selected from the group of hydrogen, an alkyl group, and an aryl group; $Y^-$ is selected from the group of a halogen, sulfate, and sulfonate; m ranges from 1 to 500, and n independently ranges from 1 to 30.

2. The emissive dendrimer composition of claim 1, further comprising a luminophore.

3. The emissive dendrimer composition of claim 2, wherein the luminophore is selected from the group of organic dyes; inorganic dyes; phosphors; semiconducting nanoparticles; pigment particles containing luminescent dye molecules, oligomers, or polymers; and mixtures thereof.

4. The emissive dendrimer composition of claim 2, wherein the luminophore is selected from the group of 4,4-difluoro-4-bora-3a,4a-diaza-s-indacene (BODIPY) dye, a rhodamine dye, a fluorine dye, a sulforhodamine dye, and mixtures thereof.

5. The emissive dendrimer composition of claim 2, wherein the luminophore is miscible with the emissive dendrimer.

6. The emissive dendrimer composition of claim 1, further comprising a polymer wherein the emissive dendrimer is miscible with the polymer.

7. The emissive dendrimer composition of claim 1, wherein the emissive dendrimer absorbs electromagnetic radiation having a wavelength in the range of 300 nm to 800 nm.

8. The emissive dendrimer composition of claim 1, wherein the emissive dendrimer emits light at a wavelength from 600 nm to 800 nm corresponding to a red color, emits light at a wavelength from 500 nm to 600 nm corresponding to a green color, or emits light at a wavelength from 400 nm to 500 nm corresponding to a blue color.

9. The emissive dendrimer composition of claim 1, wherein the emissive dendrimer is soluble in water and/or alcohol.

10. A luminescence-based sub-pixel, comprising:
a light shutter with adjustable transmission;
a luminescent layer containing a matrix including an emissive dendrimer;
a mirror for reflecting light emitted from the emissive dendrimer;
wherein the luminescent layer is disposed between the light shutter and the mirror; and
wherein the emissive dendrimer has the structure:

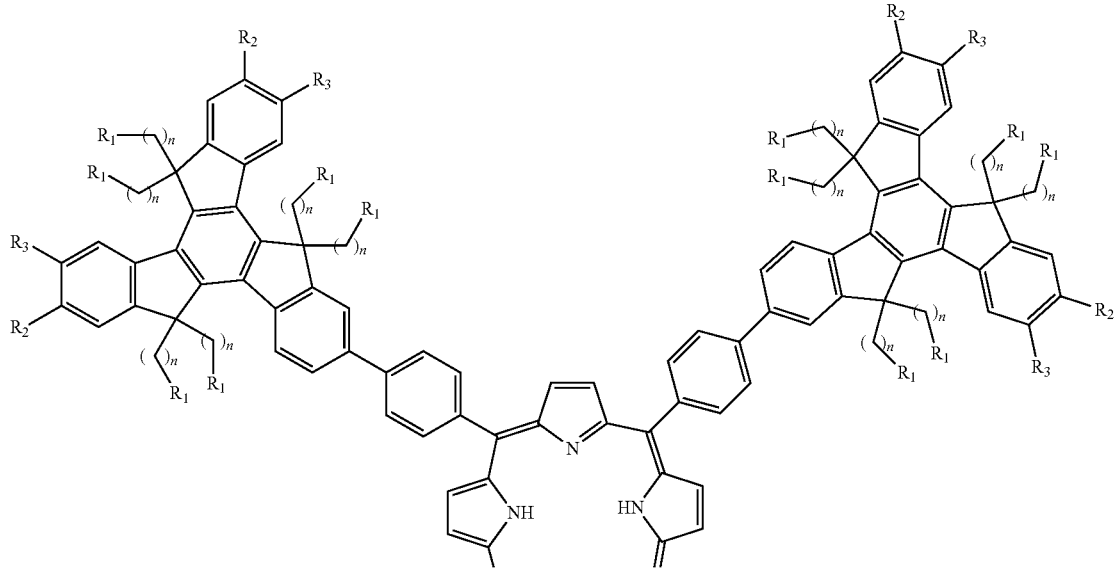

-continued

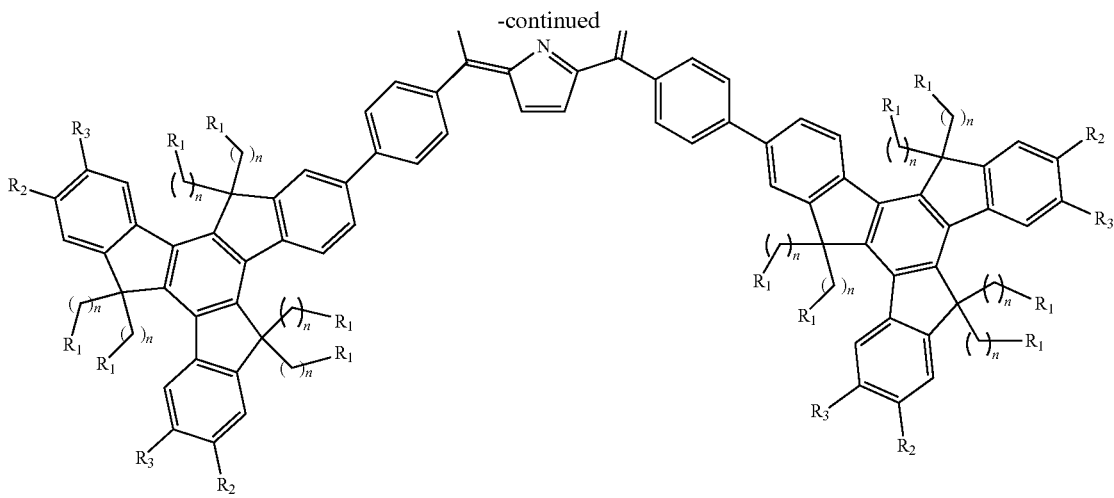

where $R_1$, $R_2$, and $R_3$ are independently selected from the group of $COOZ$, $SO_3Z$, $PO_3Z$, $N(R)_3{}^+Y^-$, and $(CH_2CH_2O)_mCH_3$; Z is independently selected from the group of hydrogen, a monovalent metal ion, and $N(R)_4{}^+$; R is independently selected from the group of hydrogen, an alkyl group, and an aryl group; $Y^-$ is selected from the group of a halogen, sulfate, and sulfonate;

m ranges from 1 to 500, and n independently ranges from 1 to 30.

11. The luminescence-based sub-pixel of claim 10, wherein
the matrix further comprises a luminophore selected from the group of organic dyes; inorganic dyes; phosphors; semiconducting nanoparticles; pigment particles containing luminescent dye molecules, oligomers, or polymers; and mixtures thereof; and
the mirror reflects light emitted from the luminophore.

12. The luminescence-based sub-pixel of claim 11, wherein the emissive dendrimer absorbs energy in the form of electromagnetic radiation and transfers the energy to the luminophore.

13. The luminescence-based sub-pixel of claim 10, wherein the luminescence-based sub-pixel is part of a reflective display.

14. A luminescence-based pixel comprising three luminescence-based sub-pixels of claim 11, wherein each luminescence-based sub-pixel corresponds to a different color of emitted light such that the luminescence-based pixel can emit light over a spectrum of 300 nm to 800 nm.

15. A method of illuminating a display, comprising:
dispersing an emissive dendrimer in a luminescent layer, wherein the emissive dendrimer has the structure:

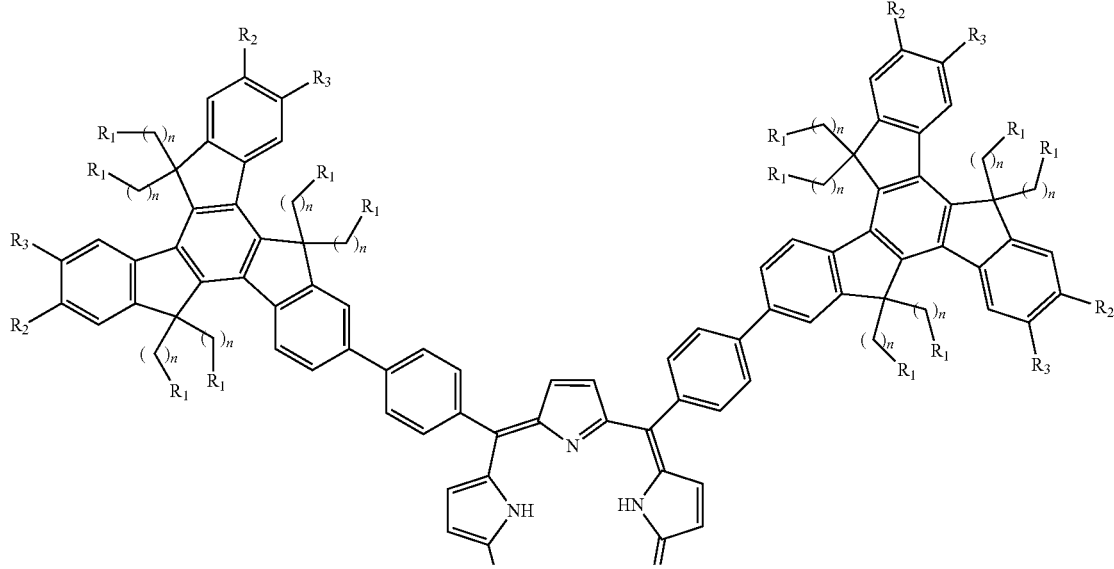

-continued

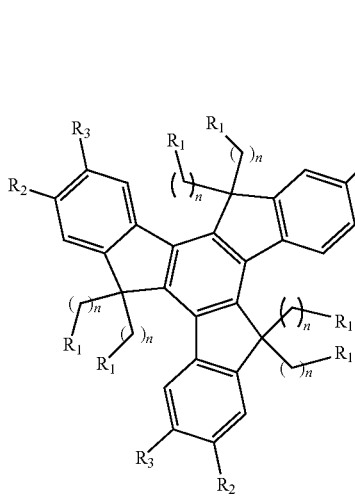
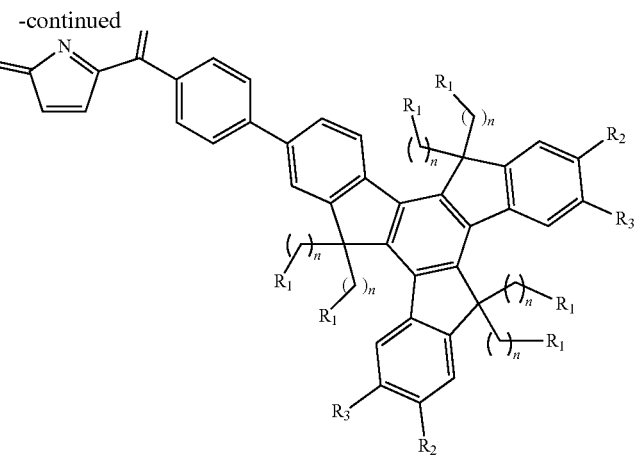

where $R_1$, $R_2$, and $R_3$ are independently selected from the group of $COOZ$, $SO_3Z$, $PO_3Z$, $N(R)_3{}^+Y^-$, and $(CH_2CH_2O)_mCH_3$; Z is independently selected from the group of hydrogen, a monovalent metal ion, and $N(R)_4{}^+$; R is independently selected from the group of hydrogen, an alkyl group, and an aryl group; $Y^-$ is selected from the group of a halogen, sulfate, and sulfonate; m ranges from 1 to 500, and n independently ranges from 1 to 30; and exposing the luminescent layer to electromagnetic radiation.

* * * * *